United States Patent [19]

Hoy

[11] Patent Number: 4,573,455
[45] Date of Patent: Mar. 4, 1986

[54] KNEE ORTHOTIC HINGE JOINT

[76] Inventor: David J. Hoy, 1095 County Rd. 2256, Perrysville, Ohio 44864

[21] Appl. No.: 564,507

[22] Filed: Dec. 22, 1983

[51] Int. Cl.[4] ............................................. A61F 5/04
[52] U.S. Cl. ...................................... 128/80 C; 128/88
[58] Field of Search ................ 128/80 R, 80 C, 80 F, 128/88, 87 R

[56] References Cited

U.S. PATENT DOCUMENTS

| | | | |
|---|---|---|---|
| 3,528,412 | 9/1970 | McDavid | 128/80 C |
| 3,669,105 | 6/1972 | Castiglia | 128/80 C |
| 3,885,252 | 5/1975 | Nakajima | 128/80 C |
| 4,064,874 | 12/1977 | Valin | 128/80 C |
| 4,130,115 | 12/1978 | Taylor | 128/80 C |
| 4,144,881 | 3/1979 | Chappell | 128/80 R |
| 4,245,629 | 1/1981 | Cummins | 128/80 C |
| 4,361,142 | 11/1982 | Lewis et al. | 128/80 C |

FOREIGN PATENT DOCUMENTS 79821  6/1919  Austria ............................ 128/80 C

OTHER PUBLICATIONS

Pamphlet produced by Omni Scientific, Inc., describing the "Anderson Knee Stabler".
Foster, R. and Milani, J., "The Genucentric Knee Orthosis—A New Concept", Orthotics and Prosthetics, 33, 1979, 31-34.
Lew, et al., "A Comparison of Pistoning Forces in Orthotic Knee Joints", Orthotics and Prosthetics, 36, 1982, 85-95.

Primary Examiner—John D. Yasko
Attorney, Agent, or Firm—Woodling, Krost & Rust

[57] ABSTRACT

An orthopedic hinge joint mechanism to maintain knee stability and to protect the unstable and injured knee. Said hinge is comprised of two upright members articulating with two additional offset linkage pieces. This system is utilized separately or in conjunction to provide limited and controlled motion in the anatomical sagittal and frontal planes. It is covered with a flexible tubing and appropriately affixed to one or both sides of the affected limb to resolve instability of the knee due to ligamentous rupture or laxity.

4 Claims, 6 Drawing Figures

KNEE ORTHOTIC HINGE JOINT

This invention relates to improvements in knee joint orthoses. In particular, it relates to a hinge joint mechanism of compact construction which will follow the complex motion of the normal knee but prevent harmful forms of knee joint motion.

BACKGROUND OF THE INVENTION

Knee braces and hinge systems are commonly externally affixed to the lower extremity to stabilize the injured, unstable, and painful knee. Traditional application of knee orthotic hinges, joints, and devices have encountered established problems. In an attempt to stabilize the human knee and match the complex motion it presents, prior designs have compromised functional usage in regard to athletics and activities of daily living.

To provide support and stability the device must transmit certain mechanical forces that counteract and balance the abnormal forces present which are initiating the instability and that result in pain and deformity. The mechanical principles that correct the deformity and prevent injury/re-injury have long been identified and are well understood. It is the transmission of these correcting and stabilizing forces to the human tissue at tolerable levels that remains unsolved by prior art.

In addition, prior art has attempted to resolve the long standing problem of providing stability to the injured and unstable knee while at the same time avoiding rotation and loss of suspension of the device with resultant skin abrasions and abnormal stresses to the knee due to the inability of the device to match normal kinematics of the human knee. Current designs such as the Genucentric Knee Hinge and the Northwestern Knee Orthosis (U.S. Pat. No. 4,361,142) have established claim to resolution of these problems.

Existing devices suffer the disadvantages of excessive bulk, weight, and the inability to match the functional anthropometric contours of the human extremity. Many also fail to apply necessary corrective and supportive total contact forces. Total or full contact forces are required to bring corrective pressures within reasonable, tolerable levels. It is known that Pressure=Force/Area ($P=F/A$). The greater the area over which a force is distributed, the less the pressure resulting from a given force. Body weight and activity forces are of a large magnitude but nevertheless pressure must be applied at tolerable levels.

Because these problems remain unresolved in the prior art, many devices are subjected to a high rate of user/wearer rejection.

Often, bilateral involvement (that is, of both knees) occurs. With prior art, the protruding bulk of the componentry impedes normal bipedal activity and functional efficient gait is impaired. The resultant poor cosmesis of the devices adds to the high user/wearer rejection rate. Bilateral involvement requires a low profile design which does not significantly increase the girth and circumference dimensions of the device.

Another failing of many prior art devices is the failure to restrict extension of the lower leg at the knee joint. Current orthopedic surgical management mandates limited excursion of extension or approximately 10° to 20° of terminal extension to protect surgical reconstruction. This corresponds to 170°-160° of extension of the knee joint.

SUMMARY OF THE INVENTION

The hinge system of my invention is a true polycentric multi-axial articulating joint component that has the ability to match normal kinematic motion of the knee joint. The flexion-extension motion of the knee is best described as a rolling and gliding movement which should be accurately followed by the bracing structure. Since this normal complex human motion is unique to each individual, support must not be constrained to a simplistic path.

A bracing structure employing my hinge mechanism allows three or more pivotal and rotational points to coincide with the normal kinematic function of the knee in regard to the motion of flexion and extension. With my invention, any component member may rotate about the respective fixed axis with regard to the adjacent member. This singular rotation when translated to the adjacent component member provides a combination of motion that replicates the normal kinematic function of the knee. It is this singular motion when combined with the additional range of the pivotal members that allows the complex rotation-translation of the lower leg with respect to the upper leg. My device, unlike many in the prior art, does not attempt to guide or follow the geometry of the articular surfaces; rather, it allows the pure range of normal motion to remain free and unimpeded. However, it restricts not only abnormal motion but also extension of the lower leg beyond appropriate physiological limits.

Both these aims are achieved by means of an extraordinarily compact and trouble-free construction. Thus the weight and bulk characteristic of much of the prior art is avoided, and my hinge may be used, either singly or in pairs, in a variety of brace constructions. Equally importantly, because of its compact componentry, the hinge can be directly contoured and applied to the anthropometric outline of the individual knee, providing full and total contact, with maximum support, against the skin. In this way, unwanted abnormal forces, motion and abrasions are prevented, and corrective and supportive forces are applied directly to the region of instability.

Although the hinge system itself is comprised of a substantially strong, rigid, and durable material, it is preferably covered with a pliable rubber sheath tubing which serves several purposes.

Drawn over the contoured hinge, the tubing acts as a comfortable padded interface liner which allows direct contoured contact against the skin to apply forces which protect the knee from injury or re-injury. This minimizes injury and abrasions to the wearer or other athletic participants who may be exposed to the hinge in sports. It also acts as a sealed joint system to prevent foreign matter from interfering with the mechanical action of the hinge system, and allows sealed lubrication of the hinge. The functional mechanical lifetime of the hinge is thus prolonged.

The external tubing also provides a supportive force to evenly guide and permit smooth unimpeded motion to the internal hinge system.

Accordingly, it is one object of this invention to provide a hinge system that effectively mimics the complex anatomical motion of the human knee while preventing undesired motions.

Another object of the invention is to allow corrective forces to be applied directly to the knee without undue discomfort.

Yet a further object of the invention is to provide a compact hinge system of low weight and bulk which because of its simplicity is not susceptible to mechanical failure and is versatile in application.

That these and other objectives have been achieved will be apparent from the following detailed description and claims, taken in conjunction with the figures herein, in which:

DETAILED DESCRIPTION OF A PREFERRED EMBODIMENT

Figure 1:
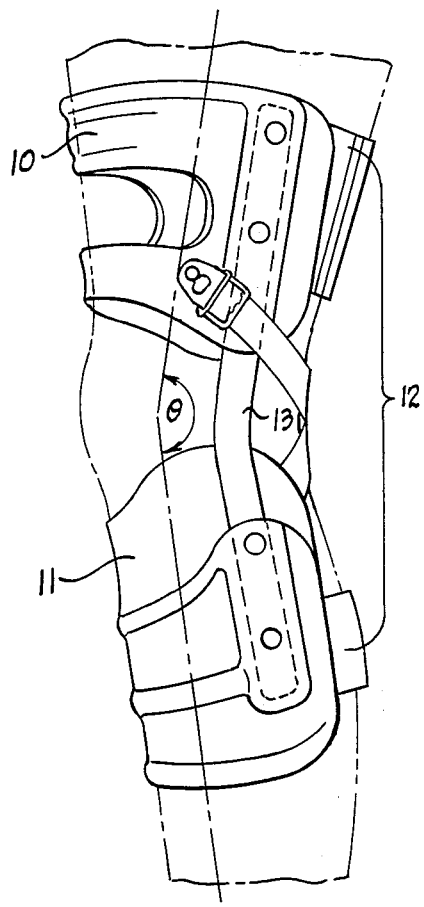
FIG. 1 is a perspective view of the hinge mechanism of my invention incorporated into a typical rigid knee orthosis with the tubing covering the hinge mechanisms.
Figure 5:
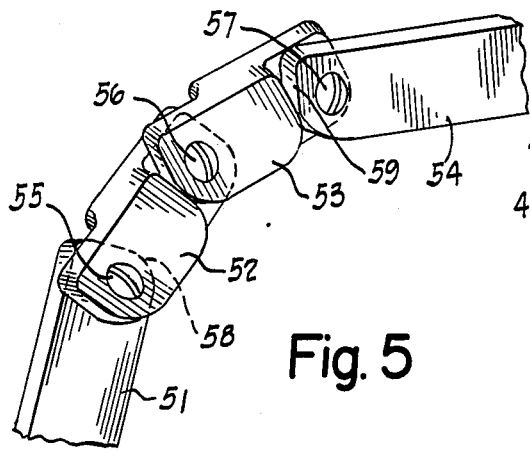
FIG. 5 is a perspective view of the central portion of the hinge mechanism, showing the interaction of the linkage members.

FIGS. 1 and 5 are most illustrative of the preferred embodiment to be described herein. FIG. 1 shows a typical complete knee brace structure comprising a first or upper leg brace portion 10, a second or lower leg brace portion 11, and the hinge mechanism 12 of the subject invention firmly affixed alongside the knee to the brace portions. In FIG. 1, the hinge mechanism 12 is shown covered by tubing 13. Ordinarily, there will be two such hinge mechanisms, one on each side of the wearer's knee.

The leg brace portions 10 and 11 may be of any conventional construction which permits firm affixation of the upper and lower portions of the hinge mechanism to them, and also permits them to be firmly bound to their respective leg portions. I have found that padded shells of a thermoplastic substance such as polypropylene or polyvinyl chloride, fastened by various of the strapping means well known to those skilled in the art, are sufficient.

In one alternative embodiment, not pictured, the hinge mechanism 12 may be inserted into sewn-in pockets in one-piece knee supports, such as the elastic ones commonly used where a large brace is not needed. In that case a lighter and thinner version of the hinge mechanism, not covered by the tubing 13 of the preferred embodiment, may suffice.

If a leg brace such as that in FIG. 1 is used, the elongated arm members 51 and 54 are provided with holes or other means for firm fastening of the ends of the hinge mechanism to the brace. In other applications, such as insertion into lighter supports, members 51 and 54 need not be elongated, and it is only necessary that measures be taken to prevent the twisting of the hinge mechanism in the pocket containing it.

Figure 2:
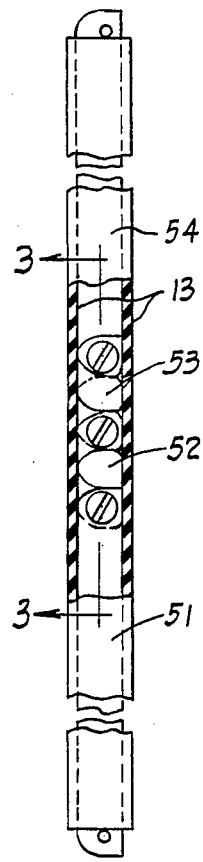
FIG. 2 is a side elevation, shown in section, of the hinge mechanism.
Figure 3:
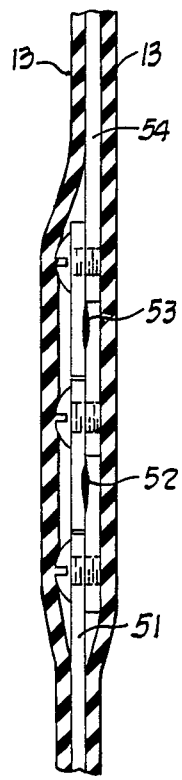
FIG. 3 is a front elevation, shown in section, as taken through lines 3—3 of FIG. 2.

The hinge mechanism 12 itself is best seen in FIGS. 2, 3 and 5. The hinge mechanism consists of elongated arm members 51 and 54, shown with their outer portions cut away in FIGS. 3 and 5, and central linkage members 52 and 53.

In FIGS. 2 and 3 the tubing 13 is also seen in section. This tubing can be fabricated from a number of materials such as vinyl, polyvinyl chloride or pure gum rubber. The tubing guides the articulating members of the hinge system in a uniform motion allowing an even transition of rotation to occur.

As viewed in FIG. 1, the hinge can be applied directly to the skin tissue contours of the extremity, because of the cushioned effect provided by the tubing. This cushioned effect not only protects the wearer of the device but aids in protection of other participants in athletic competition.

Preferably, the tubing runs full length of the bracing structure and is sealed at both ends. This provides sealed lubrication and extended mechanical life while at the same time prevents debris from entering the articulating mechanical structure.

Fundamental to my invention is the construction of the hinge mechanism 12. It will be seen that the members 51 through 54 have parallel planar surfaces provided with holes, so that they may be hingedly connected one to another at 55, 56 and 57 with the axes of rotation of adjacent members all parallel. In this way the mechanism as a whole permits member 51 to have a component of rotation with respect to member 54 parallel to the same axis. Since there are more than one intermediate rotational connections, a translational component in the same plane is also possible. It is this combination which permits the hinge mechanism to follow the knee joint motion, which is substantially, but not exactly, rotational in nature.

Figure 4:
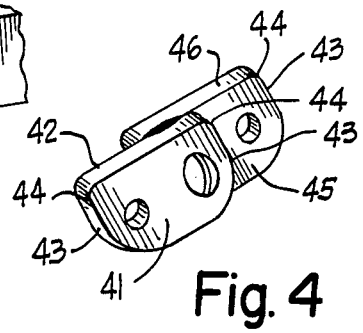
FIG. 4 is a perspective view of a single central linkage member.

Another feature of this embodiment is seen in the shape of the central linkage members 52 and 53. A single such member is shown in FIG. 4. It has a lower plate section 41 with opposed parallel surfaces, and a lower side wall 42 shaped generally as a semi-circle having a flattened portion 43 of its arc, and a corner 44 on each end. A similar upper plate section 45 has a similarly shaped upper side wall 46, with similar areas 43 and 44. Plate sections 41 and 45 are joined at opposed parallel surfaces, for example, by welding or by a permanent bolt as in FIG. 4. (If a bolt is used, it must not permit rotation of the plate sections with respect to each other.) Holes 47 and 48 are provided so that rotational connections at 55, 56 and 57 may be made by bolts or the like.

Lower elongated arm member 51 has an upper end 58 shaped similarly to the upper portion of upper plate section 45, while upper elongated arm member 54 has a lower end 59 shaped similarly to the lower portion of lower plate section 41.

The shape of members 51 through 54, as described and pictured, allows for two features. First, since the plate sections 41 and 45 are offset from each other, members 51 through 54 nest compactly together. The hinge mechanism is thus flat enough to lie closely next to the knee joint. The second feature is the shape of sidewalls 42 and 46, and their corresponding walls on the arm member ends 58 and 59. These side walls are rounded to permit some rotation at axes 55, 56 and 57, but at portions 43 and 44 the radii of curvature increase so that opposing sidewalls make contact and may not rotate past one another as the leg reaches a certain angle of extension (angle $\theta$ of FIG. 1).

The shapes of portions 43 and 44 of the sidewalls may be adjusted so that the sum of all the rotational arcs at axes 56 through 57 are equal to or less than 180° of motion, or any other desired total angle. In practice, current orthopedic knee rehabilitation management requires that certain limitations be placed upon the final degrees of extension or 160° to 170° of terminal extension. This demands variable adjustability in a bracing structure. By permitting an increase of 2°–4° at the top radius of each articular contact stop, the bracing structure achieves this variable adjustability. My practice has been to manufacture the sidewalls so that only a total rotational arc of 160° (or even less extension) is possible. The hinge mechanism may then be adapted to permit any prescribed greater angle of extension by grinding off portions of sidewall areas 43 and 44.

Figure 6:
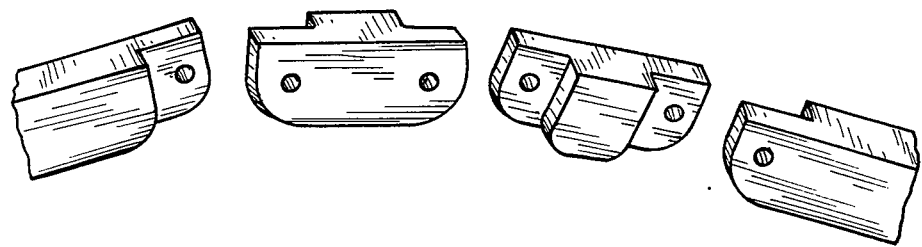
FIG. 6 is an exploded perspective view of an alternate embodiment of the hinge mechanism.

It will be seen that while the particular construction shown in FIGS. 2 through 5 is convenient to manufacture, the same principles may be employed in alternate constructions. FIG. 6, for example, shows another embodiment in exploded view. In general the practice of my invention requires that there be at least three parallel axes of independent rotation of hinge members with respect to each other, in order to follow the knee joint motion. It also requires that there be means to restrict the possible angle of rotation in each hinge joint to lie within some angle between 0° and 180°, the sense of all such angles being taken in the same direction so that the total rotational angle between the end pieces of the hinge mechanism is also no more than 180°. In these examples, the angular restriction is achieved by the contact and mutual interference of opposed wall means, but in general any standard mechanical means for limiting the range of pivot or rotation of one member about another, usually by the contact and interference of portions of the respective members, will suffice.

Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and the scope of the invention as hereinafter claimed.

What is claimed is:

1. A hinge mechanism for following the motion of the human knee, said hinge mechanism comprising first, second, third and fourth hinge members, said first hinge member being rotatably connected to aid second hinge member by a first hinge pin member at a first axis of rotation, said second hinge pin member being rotatably connected to said third hinge pin member by a second hinge pin member at a second axis of rotation, said third hinge member being rotatably connected to said fourth hinge member by a third hinge pin member at a third axis of rotation;

each said rotatable connection permitting rotation about its said axis of rotation independently of any other said rotatable connection;

said first, second and third axes of rotation being substantially mutually parallel lines so that the directions of rotation of each said hinge member, with respect to any other said hinge member rotatably connected to it, all are substantially parallel to the same plane of rotation;

means for restricting the angle of rotation between each two said rotatably connected hinge members to lie within 0° to 180°, as viewed from one side of said plane of rotation; said means comprising opposing sidewalls on each two said rotatably connected hinge members, which said opposing sidewalls contact each other when a predetermined angle of rotation is reached, thereby preventing rotation beyond said predetermined angle of rotation; and said hinge mechanism further comprising a length of flexible tubing extending over and encasing the rotatable connections of said mechanism in the regions of said rotatable connections.

2. A hinge mechanism for a knee joint supporting device, said hinge mechanism comprising the mechanism of claim 1 and in which said hinge mechanism is adapted to be held by said knee joint supporting device so that when said device is worn, said axes of rotation are substantially parallel to the normal axis of rotation of the wearer's lower leg about his upper leg at the knee joint.

3. A hinge mechanism for a knee joint supporting device, said hinge mechanism comprising a number n of hinge members, where n is at least four, said hinge members being mutually connected in linear series from said first to said nth hinge member, each said hinge member being rotatably connected to said next hinge member by a hinge pin member at an axis of rotation;

each said rotatable connection permitting rotation about its axis of rotation independently of any other said rotatable connection;

all said axes of rotation being substantially mutually parallel lines to that the directions of rotation of each said hinge member, with respect to any other said hinge member rotatably connected to it, all are substantially parallel to a single plane of rotation;

means for restricting the angle of rotation between any two said rotatably connected hinge members to lie within 0° to 180°, as viewed from one side of said plane of rotation, said means comprising opposing sidewalls on each two said rotatably connected hinge members, which said opposing sidewalls contact each other when a predetermined angle of rotation is reached, thereby preventing rotation beyond said predetermined angle of rotation; and said hinge mechanism further comprising a length of flexible tubing extending over and encasing the rotatable connections of said hinge mechanism in the regions of said rotatable connections.

4. The hinge mechanism of claim 3 and in which said first and nth hinge members are adapted to be rigidly affixed to first and second portions, respectively, of said knee joint supporting device such that when said device is worn, said axes of rotation are substantially parallel to the normal axis of rotation of the wearer's lower leg about his upper leg at the knee joint.

* * * * *